United States Patent
McCormick et al.

(10) Patent No.: US 6,613,211 B1
(45) Date of Patent: Sep. 2, 2003

(54) CAPILLARY ELECTROKINESIS BASED CELLULAR ASSAYS

(75) Inventors: Randy M. McCormick, Santa Clara, CA (US); Gary J. Ciambrone, Redwood City, CA (US); Ian Gibbons, Portola Valley, CA (US)

(73) Assignee: Aclara BioSciences, Inc., Mountain View, CA (US)

(*) Notice: Subject to any disclaimer, the term of this patent is extended or adjusted under 35 U.S.C. 154(b) by 190 days.

(21) Appl. No.: 09/642,607

(22) Filed: Aug. 17, 2000

Related U.S. Application Data (60) Provisional application No. 60/151,150, filed on Aug. 27, 1999.

(51) Int. Cl.$^7$ .............. C02F 1/40; C02F 11/00; C25B 11/00; C25B 13/00; C25B 9/00; G01N 27/27; G01N 27/403; G01N 27/453
(52) U.S. Cl. .............................. 204/601
(58) Field of Search ........................ 204/601

(56) References Cited

U.S. PATENT DOCUMENTS

| | | |
|---|---|---|
| 5,049,673 A | 9/1991 | Tsien et al. |
| 5,260,192 A | 11/1993 | Russell et al. |
| 5,436,128 A | 7/1995 | Harpold et al. |
| 5,578,460 A * | 11/1996 | Ebersole et al. .......... 204/451 |
| 5,789,167 A * | 8/1998 | Konrad ...................... 435/6 |
| 5,843,680 A | 12/1998 | Manian et al. |
| 5,858,195 A | 1/1999 | Ramsey |
| 5,876,675 A | 3/1999 | Kennedy |
| 5,897,990 A | 4/1999 | Baumann et al. |
| 5,900,130 A * | 5/1999 | Benvegnu et al. ......... 204/453 |
| 5,958,202 A * | 9/1999 | Regnier et al. ............ 204/451 |
| 5,993,631 A * | 11/1999 | Parton et al. .............. 204/547 |
| 6,013,165 A * | 1/2000 | Wiktorowicz et al. ..... 204/456 |
| 6,120,666 A * | 9/2000 | Jacobson et al. .......... 204/452 |
| 6,297,061 B1 * | 10/2001 | Wu et al. ................. 210/198.2 |

FOREIGN PATENT DOCUMENTS

| | | |
|---|---|---|
| WO | WO 98/00231 | 1/1998 |
| WO | WO 98/10267 | 3/1998 |
| WO | WO 98/43066 | 10/1998 |
| WO | WO 98/46438 | 10/1998 |

OTHER PUBLICATIONS

Jardemark, Kent, et al., "Screening of Receptor Antagonists Using Agonist–Activated Patch Clamp Detection in Chemical Separations", *Anal. Chem.* 70, pp. 2468–2474, 1998.

Chiu, Daniel T., et al., "Injection of Ultrasmall Samples and Single Molecules into Tapered Capillaries", *Anal. Chem.* 69, pp. 1801–1807, 1997.

Fishman, Harvey A., et al., "Cell–to–Cell Scanning in Capillary Electrophoresis", *Anal. Chem.* 68, pp. 1181–1186, 1996.

Denecke et al., "Falsification of Tetrazolium Dye (MTT) Based Cytotoxicity Assay Results due to Mycoplasma Contamination of Cell Cultures", *Anticancer Res.* 19, pp. 1245–1248, 1999.

Pembrey, Richard S., et al., "Cell Surface Analysis Techniques: What Do Cell Preparation Protocols Do to Cell Surface Properties?", *Environ. Microbiol.* 65, pp. 2877–2894, 1999.

Li, Paul C. H. and Harrison, D. Jed, "Transport, Manipulation, and Reaction of Biological Cells On–Chip Using Electrokinetic Effects", *Analytical Chemistry*, vol. 69, No. 8, Apr. 15, 1997, pp. 1564–1568.

* cited by examiner

*Primary Examiner*—Mark L. Bell
*Assistant Examiner*—Jennine M. Brown
(74) *Attorney, Agent, or Firm*—Jacqueline F. Mahoney; Judy M. Mohr; Perkins Coie LLP (57) ABSTRACT

Cell based assays are performed in a microfluidic device, where the cells are introduced into a reservoir and are contacted with one or more agents prior to or during their residence in the reservoir or in a capillary channel connected to the reservoir. The cells are moved by electrokinesis individually from the reservoir to a detector, where the status of the cells as a result of contacting said agents is determined. Conditions are provided for moving the cells electrophoretically or by electroosmotic force, where the cells may be viable or fixed, natural or genetically modified.

15 Claims, 6 Drawing Sheets

CAPILLARY ELECTROKINESIS BASED CELLULAR ASSAYS

CROSS-REFERENCE TO RELATED APPLICATIONS

This application claims priority of U.S. Patent Provisional Application Serial No. 60/151,150 filed on Aug. 27, 1999, which disclosure is-incorporated herein by reference.

INTRODUCTION

1. Technical Field

The field of this invention is assays involving cellular response to compounds of interest.

2. Background

There are a number of different situations where one is interested in the cellular response to a compound. In the screening of test compounds, the sensitivity of aberrant or normal cells to agents, or elucidating biological pathways, there is an interest in whether a compound will bind to a receptor in the cellular environment, the transduction of a signal from a membrane into a cellular compartment, or the response of the cell to the agent. While screening compounds solely for binding provides for rapid screening capabilities, the information content is limited due to the restricted nature of the assay.

Using cells as the target for the compounds has many advantages in allowing for a more natural environment for binding, where the receptor is in its natural environment and will be associated with the membrane and other proteins, which may complex with the receptor. Where the cell is viable, there is the potential for detecting the influence of the compound on the biological pathways of the cell, which in many situations may be essential for evaluating the potential of the compound. A viable cell gives an immediate indication of toxicity of the compound and depending on the circumstances, will allow for the determination of transcription, expression, ion channel activity, and the like. Where cells have been genetically engineered, there is the further opportunity to provide for a specific target for the transduced signal, where expression produces a detectable signal, such as green fluorescent protein or an enzyme, which acts on a substrate to provide a detectable signal. Such enzymes include β-galactosidase, luciferase, etc.

In many instances, the amount of candidate compound and one or more reagents which is available is very small, being rare and/or expensive, so one wishes to have as small a reaction volume as possible. In addition, there are advantages to be able to identify the results with individual cells, so that a distribution of values is obtained, rather than a single value from a bulk medium or a value averaged over many cells.

One potential method for assaying the effect of compounds on cells is capillary electrokinesis. Concerns associated with the use of capillary electrokinesis are the maintenance of cellular viability, clumping and aggregation of cells, capillary wall adhesion, control of cellular movement and the effect of the medium on the binding of compounds to their respective receptors and transport across the cellular membrane. Particularly, as to viability, the saltconcentrations employed for cell media are drastically higher than are useful for electrokinesis. However, the advantages of being able to move small volumes of predetermined volume and concentration, permitting relatively high concentrations with small amounts of materials, detecting the effects on individual cells and being able to do numerous determinations simultaneously, makes the use of capillary electrokinesis an attractive opportunity.

3. Brief Description of Relevant Art

WO98/002321 describes a microfluidic apparatus for high throughput screening. U.S. Pat. No. 5,843,680 describes an apparatus for analyte detection. U.S. Pat. No. 5,260,192 describes an apparatus for screening cells. WO98/10267 and 98/43066 describe microflow systems for separating particles. U.S. Pat. No. 5,876,675 describes a microfluidic device for performing experiments including cell separation. The Zare group has published a number of papers concerning transport of analytes using capillary electrophoresis for cellular assays. See, for example, Jardemark, et al., Anal. Chem. 1998, 70, 2468–2474; Chiu, et al., ibid 1997, 69, 1801–1807; and Fishman et al., ibid, 1996, 68, 1181–1186.

SUMMARY OF THE INVENTION

Cellular operations are performed in a microfluidic device, employing a reservoir of cells, moving cells individually from the reservoir into a capillary channel by means of electrokinesis, contacting individual cells with one or more appropriate agents under conditions for performance of the operation and determining the results of the operation. Viable cells, particularly mammalian cells, may be employed in the process in a viability-maintaining environment or fixed cells may be used in media which are not restricted as to composition.

DESCRIPTION OF THE SPECIFIC EMBODIMENTS

Cellular operations are performed in a microfluidic device, whereby cells of interest are introduced into a reservoir of a microfluidic device. The reservoir is connected to a channel or other reservoirs, which channel may have branches and connections to other channels, where the channels will be subject to electrokinetic forces for movement of the cells in the channels and for contacting the cells with agents for performance of an operation. The cells can be moved in small discrete groups or individually from the reservoir into a channel and processed in accordance with the operation and the result of the operation then determined. A detector is provided which views the medium at a site in the channel to determine the status of the cells as a result of the interaction with the agent(s). By "status" is intended any change in a characteristic of the cell, which can be detected, including the binding of agents, changes in physiologic pathways, viability of the cells, mitotic status, shape, etc.

Using electrokinesis, there are three ways to move cells in capillary channels: electrophoresis, electroosmotic force and electroosmotic pumping. In the case of electrophoresis, the cells will be subject to an electrical field and desirably a low salt concentration buffer will be used to prevent overheating that would occur in a high salt medium, which is the medium desired for viable cells. In this situation, one will normally use fixed cells, which will retain their receptor binding characteristics in the low salt medium and may be transported in the channel based on their mass/charge ratio. For moving the cells by electroosmotic force, again the cells will be subject to an electrical field, but the movement of the cells will be driven by the electroosmotic force, so the cells will move both as a function of their charge and the electroosmotic flow which is independent of the cellular charge. The electroosmotic pump is connected to the cell channel, where the cell channel is not in an electrical field. By having fluid flow in the pump in one or two legs, where the flow is directed away from the cell-containing channel, the cells can move toward the electroosmotic pump along with any reagents in a medium appropriate for cell viability.

The cells may be subjected to different buffers, depending upon the nature of the cells, the operation, whether the cells are viable or fixed, the exposure time for the cells, and the like. For viable cells, one will normally employ a relatively high salt concentration as compared to the most advantageous salt concentration for electrokinesis. Therefore, when using viable cells, desirably one will use, when appropriate, phosphate buffered saline, HEPES, MOPS, Tris, etc., pH 7.0 to 7.5, where the salt concentration, e.g. NaCl, KCl, etc., will generally be at least about 100 mM and not more than about 200 mM. In addition, from about 5–20% fetal calf serum or other proteinaceous composition may be present. By contrast, the salt concentration for electrokinesis will generally be below about 100 mM, since at higher conductivities the voltage has to be relatively low to prevent overheating the capillary and consequently the movement of charged species is slower. For the electrokinesis, one would prefer to have a low conductivity and work at about 10 to 50 mM salt.

The parameters to be considered are the desired speed of the operation, the viability of the cells, the susceptibility of the cells to lower salt concentrations, the effect of the addition of agents to increase osmotic pressure of the buffer medium, whether electrophoresis or electroosmotic force ("EOF") is being used, where the latter may be distant from the area of the cellular operation, the duration of the operation where the cells are exposed to the non-physiologic osmolality, and the like. To maintain osmolality or an isotonic medium, one may use neutral compounds, including zwitterions, which are physiologically acceptable. Such compounds include saccharides, e.g. glucose, dextran, cyclodextrin, etc., urea, polyalkylene oxides, polyols, betaines, cholines, silanols, etc. The concentration of the osmolality enhancing agents will vary with the agent to provide a physiologic osmolality in the range of about 250 to 350 mOsm.

For the use of electrophoresis for movement of the cells, the medium will usually be non-physiologic, that is the buffer salt concentration will be marginal or less than is normally used in growth media for cells. Electrophoresis will preferably be used for fixed cells. Most cells are negative, so that the downstream electrode will be positive. Depending on the nature of the agents, they may be combined with the cells in the reservoir, introduced into a channel from a branched channel, where the branch is positioned to encounter the cells at a cross-section, to overtake the cells, as they migrate down a channel, or encounter the cells by moving in the opposite direction of the cells in the channel. Alternatively, one may provide for the agent(s) to be in the medium, so that there will be a substantially uniform concentration of the agent(s) throughout the channel network.

In one application of electroosmotic force for movement of the cells, an electroosmotic pump is employed to move the cells from one site to another. By using the electroosmotic pump, the salt medium for the viable cells may be maintained in the range of 100 to 200 mM, while the salt medium in the electroosmotic pump will be in the range of about 10 to 50 mM. The pump may be created by having at least three legs (channels), where two legs with oppositely charged walls are connected at the same site to the channel in which the cells are to be moved. Alternatively, the walls may be may be neutral or slightly charged and a charged polymer employed which provides for dynamic coating of the walls. This will be discussed in greater detail later.

The connection of the channels may be a T-shape, a Y-shape, or X-shape, where any one of the arms may be selected as the channel in which the cells are moved. In addition, there may be a channel for the cells and one or more channels for reagents to mix with the cells in the main channel. All of these channels would be subject to the EOP and be pulled together into a main channel which would move the cells to the detector.

The walls of the channels of the EOP may be charged as a result of the composition of the walls, where neutral walls may be modified to obtain the desired charge or the substantially permanent coating of the walls with polymeric compositions of a particular charge or by "dynamic" coating of the walls. For a description of an EOF pump using different forms of charged walls, see WO 98/46438 and U.S. Pat. No. 5,858,195, which are specifically incorporated herein by reference. Methods taught for providing charged surfaces are the use of detergents with a partially solubilized polymeric wall, modifying or derivatizing the polymeric surface, either chemically or by plasma irradiation, etc., coatings, and the like. The surface should have a zeta potential to provide an electroosmotic mobility (pEO) of at least about $2 \times 10^{-5}$ cm$^2$V$^{-1}$s$^{-1}$, more usually at least about $5 \times 10^{-5}$ cm$^2$V$^{-1}$s$^{-1}$. ($\mu$EO=v/E, where v is the velocity of the fluid and E is the electric field strength; Q=vA, where Q is the volume velocity of the fluid and A is the cross-sectional area of the channel through which the fluid is flowing.) By having two legs in the EOP, each leg pumping fluid from the cell channel, one can more rapidly move the cells down the cell channel. The channels associated with the pump will have a cross-section, which is capable of accommodating the flow of liquid in the different channels associated with the cells and the reagents.

With neutral polymers, such as polymethyl methacrylate, which finds extensive use, the surface may be modified by use of alkali, which results in hydrolysis of some of the ester groups, providing the negatively charged carboxy groups. The degree of hydrolysis may be controlled by the contact time, so that a zeta potential may be achieved to provide the desired flow rate. With glass and silicon walls, one has an intrinsically negatively charged wall. For positively charged surfaces, one may use positively charged polymers, such as proteins, amino-substituted polymers, choline- or betaine-substituted polymers, such as non-water soluble polyvinyl alcohol/ethers, polyacrylates, etc. The polymers may adsorb to the surface, so as to be substantially permanent during the electrokinetic operations or may be made permanent, by covalently bonding the polymer to a functionalized surface, which is activated for covalent bonding between the polymer and the channel wall. The amount of the polymer coating can be selected to provide the desired electroosmotic mobility.

Alternatively, a dynamic coating with a soluble hydrophilic polymer may be employed, where the soluble polymer is not retained by the walls and is primarily in solution. The hydrophilic polymer employed is an assemblage of repeating or monomeric units, where the monomeric units form the backbone of the polymer. The hydrophilic polymer is compatible with water, preferably water-soluble, at least to the extent that substantial EOF may be generated in an electrokinesis buffer comprising the hydrophilic polymer. Preferably, the hydrophilic polymer is water soluble at ambient conditions to the extent of at least about 1 weight percent, preferably at least about 5 weight percent. The molecular weight of the polymer should be at least 5000, preferably at least about 10,000. Usually, the molecular weight is in the range of about 104 to about 107, usually, about $5 \times 10^4$ to about $2 \times 10^6$. The polymer may contain at least 20% on an atomic weight basis of heteroatoms, e.g., oxygen (O), nitrogen (N), sulfur (S), phosphorus (P) and the like. The O, N, S, or P may be bound to carbon or one or more of each other or to hydrogen to form various functional groups, which may be a charged functionality. The functional groups include, for example, carboxyl groups (carboxylic acids), hydroxyl groups, mercapto groups, carboxamides, carbamates, carboxylic acid esters, sulfonic acids, sulfonic acid esters, phosphoric acids, phosphoric acid esters, ureas, phosphoramides, sulfonamides, ethers, sulfides, thioethers, olefins, acetylenes, amines, ketones, aldehydes and nitrites, and alkyl, alkylidine, aryl, aralkyl, and alkyl, aryl, and aralkyl substituted with one or more of the aforementioned functional groups, and the like. The hydrophilic polymer may have on the average at least one hydroxyl group per 10 carbon atoms, generally ranging from about 1.1 to 8 carbon atoms, for sugars there will usually be about one oxy group per about 1 to 1.2 carbon atoms.

Generally, the number of charged functionalities on the hydrophilic polymer is limited so as to have the charged polymer to bind not more than transiently to the surface that it contacts, but great enough to provide the desired EOF. The hydrophilic polymer generally has on the average at least one charged functionality per about 100 atoms (not counting hydrogen atoms) and usually not more than one charged functionality on the average per about 12 atoms (not counting hydrogen atoms). Charged functionalities should be separated on the average by at least about 6, more usually at least about 10 atoms. Usually, there will be a low incidence of more than about 3 charged functionalities within about 18 carbon atoms. Accordingly, the charge density is usually on the average about 1 charge per about 1 repeating unit of the polymer to about 1 charge per about 60 repeating units, more usually per about 30 repeating units, of the polymer. On the average means that the number of atoms or repeating units per charge may not be the same for each set of atoms or repeating units bearing a charge but is the average number over all the sets of atoms or repeating units.

In one embodiment the hydrophilic polymer is a polyether, i.e., a polymer comprising repeating units or monomeric units connected by ether linkages. In one embodiment the polyethers are of at least about 5 kDal and may be represented by the formula:

—[(CRH)$_m$—O—(CR$^1$H)$_n$—O]$_t$— wherein R and R1 are independently H, alkyl, cycloalkyl, alkenyl, cycloalkyl ether, cycloalkyl thioether, cycloalkyl silyl ether, and the like, or may be taken together to form a ring of 5 to 7 carbon atoms, preferably, 5 to 6 carbon atoms, which ring may be substituted with one or more substituents, wherein m and n are each independently an integer of 2 to about 10, preferably, about 2 to 4, wherein m is 1 when R and R1 are taken together to form a ring, wherein t is about 2 to about 50,000, preferably, about 500 to about 15,000, and wherein the polymer may terminate in H, hydroxyl, amine, ammonium, carboxylic acid and so forth.

Alkyl means a branched or unbranched saturated monovalent hydrocarbon radical containing 1 to 30 or more carbon atoms, such as methyl, ethyl, propyl, tert-butyl, n-hexyl, n-octyl and the like. Cycloalkyl means a saturated monovalent monocyclic hydrocarbon radical containing 3–8 annular carbon atoms, such as cyclopropyl, cyclobutyl, cyclopentyl, cyclohexyl, cycloheptyl and cyclooctyl. Alkenyl means a branched or unbranched unsaturated hydrocarbon radical containing at least one ethenylic bond (carbon-carbon double bond) and 2 to 10 carbon atoms.

Substituted means that a hydrogen atom of a molecule, such as a carbon atom of a ring in the above structure, has been replaced by a substituent, which is another atom that may be a single atom or part of a group of atoms forming a functionality. The substituent is an organic radical, which may have 1 to 50 atoms other than the requisite number of hydrogen atoms necessary to satisfy the valences of the atoms in the radical. Generally, the predominant atom is carbon but may also include oxygen, nitrogen, sulfur, phosphorus, wherein the O, N, S, or P, if present, are bound to carbon or one or more of each other or to hydrogen to form various functional groups, such as, for example, carboxyl groups, hydroxyl groups, mercapto groups (thiols), phosphates, sulfates, phosphonium ions, amino and ammonium ions. Preferably, the substituent of the ring is a hydroxyl or a hydroxyl substituted with sulfate, phosphate, carboxyl, polyiminoalkylene, hydroxyl substituted polyiminoalkylene, substituted polyphosphonium alkylene, substituted polyphosphorus alkylene, and the like, where the iminoalkylenes are of from about 4 to 30 carbon atoms and have one amino group per 2 to 12 carbon atoms and from about 2 to 6 amino groups, the alkylene groups being of from about 2 to 12 carbon atoms.

Polyethers include, for example, polysaccharides, polyalkylene glycol, where the alkylenes are of from 2 to 6 carbon atoms, and the like. Preferred hydrophilic polymers in accordance with the present invention are polysaccharides. For polysaccharides the monomeric units may be one or a mixture of saccharides such as, for example, glucose, mannose, galactose, arabinose, altrose, gulose, iodose, talose and the like. The ratio of different saccharides in the hydrophilic polymer may be, e.g., about 1:1 to about 1:100. When the monomeric unit is glucose, the polymer may be, for example, a dextran and so forth. When the monomeric unit is alternately mannose and galactose, the polymer may be, for example, a guaran and so forth. Other polysaccharides include pullulans, konjacs, locust bean gum, agars, alginates, chitins, β-glucans, heparins, pectins, starches, tragacanthis gums and xanthum. In one embodiment the polysaccharide can comprise polyiminoalkylene groups linked to a hydroxyl of the saccharide monomeric unit. The number of amino groups within the polyiminoalkylene groups may be on the average about one per about 3 carbon atoms to about one per about 30 carbon atoms.

Examples of charged hydrophilic polymers of the present invention, by way of illustration and not limitation, are set forth below wherein m is the number of saccharide monomer units and n is the number of saccharide monomer on the average per substituent carrying a charge-imparting moiety. On the average means that the number of saccharide monomer units per substituent carrying charge-imparting moieties may not be the same for each set of saccharide monomer units bearing a substituent but is the average number over all the sets of saccharide monomers. Compound E where n=3 is available from Sigma Chemical Company.

Substituted AminoDextrans
A.

m = ~2810
n = 20   1
  = 15   2
  = 10   3
  = 6    4

B.

m = ~2810
n = 6

C.

m = ~2810
n = 6

D.

m = ~2810
n = 6

E.

m = ~2810
n = 6
n = 3

F.

1. n = 1 or 2          1. n = 1 or 2
   Medium, High           Medium, High

Ratio of Galactose to Mannose 1:2

The charge-imparting groups may be bound directly to the functionality or may be bound through the intermediacy of a linking group or spacer group as discussed above with respect to the substituent. The linking group may vary from a bond to a chain of from 1 to about 50 atoms, usually from about 2 to about 20 atoms, each independently selected from the group normally consisting of carbon, oxygen, sulfur, nitrogen, halogen and phosphorous. The number of heteroatoms in the linking groups will normally range from about 0 to 10, usually from about 1 to 5. The atoms in the chain may be substituted with atoms other than hydrogen in a manner similar to that described above for the substituent and consistent with the function of the linking group, namely, linking the charge-imparting group to the polymer backbone. As a general rule, the length of a particular linking group can be selected arbitrarily to provide for convenience of synthesis and the incorporation of any desired charge-imparting group. The linking groups may be aliphatic or aromatic. For the most part the linking group will be from about 2 to 10 total atoms other than hydrogen, having from about 0 to 3 heteroatoms, which are chalcogen (oxygen or sulfur), nitrogen, where the chalcogen will be present as ether or carbonyl and the nitrogen present as amino, imino or ammonium.

In one approach, for example, positively charged polymers may be synthesized by attaching groups with amine functionalities to the polymer backbone, usually by means of a functionality on the polymer backbone. Such groups may be amino-, methylamino-, ethanolamino-, dimethylamino-, diethanolamino-, diethylenetriamino, diethylaminoethyl-trimethylammonium- and other substituted ammonium-groups. For phosphonium ions such groups include, for example, methyl phosphine, dimethyl phosphine, diethanol phosphine, trimethyl phosphonium and the like. By employing polymers having a plurality of reactive functional groups, particularly, each monomer having at least one reactive functional group, and combining the polymer with a reactive species which provides a positive charge, where the ratio of reactive functionalities on the polymer to the molecules of reactive species is not greater than one, usually not greater than 0.5, depending on the efficiency of reaction, the rate of reaction and the ease of monitoring the extent of reaction. Where one monitors the reaction, the ratio may be higher than one by interrupting the reaction before completion, but the effective ratio, that amount of the reactive species that has reacted, will be less than one.

The random distribution of the charge-imparting moieties on the polymer backbone is obtained during the synthesis of the charged hydrophilic polymer. One way of achieving the random distribution involves varying the concentration of the reactive species relative to that of the polymer. For example, for introducing ammonium groups, a polysaccharide may be reacted with different concentrations (or equivalents) of ammonium epoxide to obtain a distribution of one ammonium group for 2 repeating units to one ammonium group for 20 repeating units.

One may use the dynamic coating by adding the hydrophilic polymer to the medium in the reservoir containing the cells or to a medium in the cellular channel or a channel downstream from the cellular channel and may include the polymer in the cell-containing reservoir. For the EOP, the channel through which the hydrophilic polymer containing solution will be either neutral or lightly charged, having the opposite charge to the polymer. By lightly charged is intended that the polymer is not strongly adsorbed to the wall, but is primarily partitioned in solution. As the polymer moves through such channel, electroosmotic force will occur, pumping the solution toward the electrode of the same charge as the hydrophilic polymer. While electrophoresis would direct the polymer in the opposite direction, the EOP will generally be stronger than the electrophoretic forces, so that the hydrophilic polymer will be moved in the direction of electroosmotic flow.

The use of the soluble charged polymers, as a dynamic coating of the walls or providing for EOF without remaining affixed to the walls, has many advantages. Since the concentration of the soluble charged polymers remains constant in the medium, one will have a constant flow as a result of the electroosmotic pumping. In addition, by changing the concentration of the soluble charged hydrophilic polymers, one may change the flow or pumping rate, which provides an additional parameter in conjunction with the electric field for flow control in the main channel. The solutions employed in the electroosmotic pump (EOP) can be recycled, since an additional channel can be provided downstream of the detection site of the device for disposal of the cell channel medium, where the cell medium need never enter into the leg of the EOP.

In general, an effective amount of the charged hydrophilic polymer is about 0.0015% to about 5% by weight, usually, about 0.02% to about 0.5% by weight, of the electrokinesis buffer. Binding of the charged hydrophilic polymers to a surface may be further controlled by the use of only relatively low concentrations of the polymer in the electrokinesis buffer. The pH of the electrokinesis buffer is usually about 3 to about 12, more usually, about 4 to about 10. The pH is generally chosen to optimize the EOF, which usually involves selecting the pH that results in the ionic character of the charge-imparting groups.

The electrokinesis buffer for use with the hydrophilic charged polymer may be a conventional buffer such as, for example, the Good's buffers (HEPES, MOPS, MES, Tricine, etc.), and other organic buffers (Tris, acetate, citrate, and formate), including standard inorganic compounds (phosphate, borate, etc.). Exemplary buffer systems include: (i) 100 mM sodium phosphate, pH 7.2; (ii) 20 mM tris-base, 20 mM boric acid, 2 mM ETDA, pH 8.3; or (iii) 25 mM Hepes, pH 7.5. The buffer may also contain any other material that does not interfere with the functional behavior of the buffer, the charged hydrophilic polymer, the microfluidic processing to be conducted, and so forth.

For charged walls, the surface that contacts the electrokinesis buffer, such as, e.g., inner surfaces of channels within a microfluidic device, may be activated with base before use with the electrokinesis buffer of the invention. In the presence of a basic medium, some plastic surfaces generate carboxyl groups on the surface. Glass and fused silica surfaces have silanol groups on the surface. Both carboxyl groups and silanol groups are negatively charged and this negative charge aids in ionic interaction between these groups and the positively charged hydrophilic polymers of the invention. Such ionic interaction contributes to the superior surface coverage of the hydrophilic polymers, which bind transiently to, and prevent adsorption of proteins and hydrophobic compounds to, the channel surfaces. Basic media that may be employed to achieve such activation include, for example, aqueous sodium hydroxide, potassium hydroxide, and the like. The concentration of the basic medium should be sufficient to achieve the level of activation or hydrolysis desired. Usually, the level of hydrolysis will provide an EOF under the conditions described in the Experimental section in the range of about $-3$ to $-50 \times 10^{-5}$ cm$^2$/V sec. In this regard and from another viewpoint, the level of hydrolysis should be sufficient to achieve the desired EOF.

The methods for hydrolysis are well within the skill of the artisan. For example, with inner walls that are comprised of acrylate, aqueous base, such as aqueous sodium hydroxide, may be employed at a concentration of about 0.5 to about 2M, preferably, about 1 to 1.5 M, usually at ambient conditions. The time of treatment is generally that necessary to achieve the desired level of hydrolysis. For example, treatment may be carried out at ambient temperature for about 1 minute to about 2 hours, usually, about 10 to about 60 minutes. Following treatment the inner walls may be washed to remove excess treatment solution. Desirably, the inner walls may also be rinsed with electrokinesis buffer. In some instances and depending on the nature of the surface an aqueous acid may be used to activate the surface. The nature and concentration of the acid is based on considerations similar to that described above.

The concentration of cells in the reservoir will usually be at least about $10^3$ per ml, usually in the range of about $10^4$ to $10^8$ per ml. One will usually have at least about $10^2$ cells, more usually at least about $10^3$ cells and will usually have fewer than about $10^6$ cells.

One may use viable cells, fixed cells, natural cells, cell lines, genetically modified cells, hybridomas, or the like. Genetically modified cells may provide for predetermined, including enhanced, levels of a cell surface receptor, formation of a detectable product upon effective binding of a ligand to the cell surface receptor, novel physiological pathways, immortalization, or the like. Any of the different kinds of cells may be used where binding is the endpoint, although fixed cells will be the most convenient. Cells may be readily fixed in accordance with conventional ways, using formaldehyde or glutaraldehyde or other fixatives. Genetically modified cells may be modified by providing for expression of a fusion protein, where the protein is fused to a fluorescent protein, such as green fluorescent protein, or an enzyme, which has a product providing a detectable signal, such as β-galactosidase or luciferase. See, for example, U.S. Pat. Nos. 5,436,128 and 5,897,990. Alternatively, cells may be loaded with ionic responsive dyes, such as CA responsive dyes. See, for example, U.S. Pat. No. 5,049,673.

The cells in the reservoir may be combined with various agents for incubation or reaction. Prior to, concomitant with, or subsequent to introduction into the reservoir, the cells may be exposed to one or more agents for the performance of the operation. Incubations may be carried out prior to introduction of the cells into the reservoir or while the cells are in the reservoir. Agents may be added to the reservoir to allow for equilibrium or for kinetic determinations, as appropriate. A common use of cells is to determine activity of an agent, e.g. a ligand, where the determination may be as a result of a physiological effect of the agent or a competition between the agent and a competitive labeled reagent. For example, for test compound screening, one may add to the cells, the test compound and a known ligand for a cellular receptor, concurrently or consecutively, where there may be displacement or competition for available binding sites. The cells may then be removed from the reservoir into a channel. By having a side channel, which substantially dilutes the buffer to provide a conductivity of the medium appropriate to electrokinesis, further reaction may be quenched and the extent of the reaction determined. By using a labeled ligand, and determining the level of binding of the ligand to the cell, one can evaluate the binding affinity of the test compound. Where one is interested in transduction by the binding of the test compound to a receptor, with activation of messengers and/or transcription factors, cells which provide for a detectable signal naturally or as a result of genetic modification may be employed. Where one is interested in the level of binding, the off-rate of the ligand bound to the receptor is usually slow, so that the cells may be moved to a site for detection and the time differential between reading individual cells will not significantly change the observed result.

Instead of adding the agent(s) to the cells before the cells enter a channel, the agent(s) may be added to the cells in the channel. In this way, all cells will be exposed to the agent(s) for about the same time prior to making the determination. By having one or more side channels, which comprise sources of one or more agents, different stages of the operation may be performed as the cells move through a channel or channel network. The agents may be injected into the channel as small plugs, e.g. 10 to 500 nl, where the plug will mix with the medium carrying the cells.

In carrying out the operation, EOF pumping may be employed for moving the cells from the cell reservoir into a channel and through a channel network. The cells need not be exposed to non-physiologic medium and the pump may be downstream from the cell reservoir. By pumping fluid with the EOF pump, the cells will be drawn into a channel, where agents for the operation may also be pumped into a common channel, where the agents will act on the cells. The agents may be pumped by positive pumping, so that each agent would have its own metering or the agents may be drawn into the channel by a common pump downstream from the agent source, where the mixing of the cells and agent(s) would be based on the relative sizes of the channels. By using concentrated solutions of agents, one can provide for positive pumping using low conductivity solutions, without significantly disturbing the conductivity of the medium in the channel supporting the cells.

Operations of interest include the determination of the binding affinity of a test compound to a cell surface membrane receptor. These determinations usually involve combining the test compound at one or more concentrations with a known ligand for the receptor, where the ligand is labeled to provide a detectable signal. For the purposes of the subject invention, while a wide variety of labels may be used, e.g. fluorescent, luminescent, radioisotopic, etc., for the most part fluorescent detection will be employed. Usually, the test compound and labeled ligand will be incubated with the cells for sufficient time for the two compounds to bind to available receptors. Where one is interested in weak binding test compounds, the ratio of test compound to labeled ligand, and the availability of receptor sites, will be selected to provide a range of binding of the labeled ligand related to the binding affinity range of interest. The determination may be made as an equilibrium determination or a kinetic determination. In the latter case, the agents may be present or absent in the channel during the transport of the cells to the detector.

For determining the physiological effectiveness of a test compound, where binding of the test compound results in the production of a detectable signal, the cells and the test compound are combined under binding conditions, either in the reservoir or the channel and the cells then transported to the detector. The microfluidic device allows for a number of permutations, since the cells can be incubated and then readily removed from the medium containing the test compound or can be moved while the concentration of the test compound is maintained. In the former case, one can measure the degree of attenuation of the activation of the result of binding by detecting the signal at different times, while in the latter case, one obtains a steady state value for the activation.

Other determinations may include cellular response to toxic agents. These determinations are applicable in determining the activity of a cancer therapeutic agent with cancer cells from a patient. One would combine the cancer cells from a biopsy with an agent or combination of agents and determine the effectiveness of the treatment on the viability of the cells. Various assays are available to determine viability and the subject invention allows for a determination on an individual cell basis of the effect of the treatment, where the time of exposure to the treatment may be varied. Vital dyes will mark dead cells. See, for example, Denecke, et al., Anticancer Res. 1999, 19:1245–8 and Pembrey, et al., Environ. Microbiol. 1999 65:2877–94.

Where binding of the test compound is of interest, and a competitive ligand is employed, the cell will serve to vary the observed signal as compared to the surrounding medium. The cells may serve to concentrate the labeled ligand bound to the cell or may provide a lower effective concentration of the labeled ligand as compared to the surrounding medium. By monitoring the change in signal, one can determine the presence of a cell and the amount of labeled ligand present. In addition, one can independently determine the presence of the cell, due to the light scattering by the cell, using a source of illumination for illuminating the channel and a light detector. As the cells pass the detector, one can obtain changes in signal for each cell, frequently as sharp peaks, where the labeled ligand is concentrated by the cell, as compared to the surrounding medium, or a detectable product is produced in the cell.

The microfluidic device unit, which is employed will have a plurality of reservoirs, at least two, and at least one channel. The device may have a plurality of microfluidic units, particularly where the device interfaces with a microtiter well plate. The reservoirs will serve as cell reservoirs, agent reservoirs, waste reservoirs, etc. The reservoirs will generally have volume capacities of from about 0.1 to 20 μl, more usually from about 1 to 10 μl, to accommodate the desired number of cells, the volume of agents, and waste. The reservoirs will generally have a depth of about 0.2 to 5 mm. The channels will vary in depth and width, generally having cross-sections in the range of about 100 to 10,000 $\mu m^2$, more usually about 200 to 5,000 $\mu m^2$, where the depth will generally be in the range of about 10 to 100 μm, and the width in the range of about 10 to 250 μm, where the width will generally be greater than the depth. The materials employed for the device include silicon, glass and plastics, particularly acrylates, although other materials may also be involved, as supports, heat transfer, and the like. Generally, the device will comprise a substrate and a cover, where the substrate will generally have a thickness in the range of about 25 μm to 5 mm and an adhering cover to enclose the channels, which will generally be of a thickness in the range of about 10 to 100 μm. Desirably, the surface of the substrate will be planar. Various openings may be provided in the cover or the substrate, to provide access to the reservoirs and provide access for the electrodes. The manner of use of the device is conventional.

Voltage differentials which are employed for the transport of the cells will generally be in the range of about 100 to 2000V, more usually about 100 to 1000V. Cellse may be moved at speeds varying in the range of about 10 to $10^4$ cells/min past a detection point.

The detection site may be modified to improve detection of individual cells. The cross-section of the channel may be reduced, so as to ensure that the cell as it passes through the detection site is irradiated and one obtains an accurate determination of the number of detectable labels present on the cells. Alternatively, reversibly binding molecules may be bound to a portion of the surface in the channel, which molecules may include adhesion molecules, weakly binding antibodies, lectins, etc. Other techniques may include binding magnetic particles to the cells prior to entering the detection region and sequestering the particles to the bottom of the channel, where the light may be focused at the sight where the cells are captured. Alternatively, one may use sheath flow, having the cell containing stream sandwiched between two other streams, which serve to contain the cell containing stream in a narrow channel, where the irradiating light beam extends irradiates the entire cell containing stream. If one wishes to use sophisticated optics, one may provide the irradiation beam, as a thin line crossing the stream, so that the cell will be irradiated regardless of which part of the stream the cell is in, when the cell passes the detection site.

Often, a microfluidic network is employed, which is a system of interconnected cavity structures and capillary-size channels configured with a plurality of branches through which fluids may be manipulated and processed. A cavity structure is an unfilled space, preferably, a hollowed out space in an object, such as, e.g., a planar substrate, a plate, or the like such as, for example, a well, a reservoir, an incubation chamber, a separation chamber, an enrichment chamber, a detection chamber, and the like. The cavity structures are usually present at one or both of the termini, i.e., either end, of a channel. The cavity structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like. Channels provide a conduit or means of communication, usually fluid communication, more particularly, liquid communication, between elements of the present apparatus. The elements in communication are, e.g., cavity structures, and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoid, square, rectangular, triangular and the like so that it forms a microchannel within the substrate in which it is present.

The channels and the like are usually of capillary dimension, i.e., having a cross-sectional area that provides for capillary flow through a channel. At least one of the cross-sectional dimensions, e.g., width, height, diameter, is at least about 1 μm, usually at least 10 μm, and is usually no more than 500 μm, preferably no more than 200 μm. Channels of capillary dimension typically have an inside bore diameter (ID) of from about 1 to 200 microns, more typically from about 25 to 100 microns, with cross-sections of greater than 100 microns, generally in the range of about 250 to 5000 microns.

The following examples are offered by way of illustration and not by way of limitation.

EXPERIMENTAL

In the first study, KNRK cells (Kirsten normal rat binding cells), transfected with the neurokinin gene were fixed by lifting cells off the flask with PBS (without $Ca^{2+}$ or $Mg^{2+}$) at 37° C. for 10 min, in a bang flask. After spinning down (1000 rpm, 5 min), the cells were resuspended in PBS, placed on ice and counted in a hemocytometer. The cell concentration was adjusted to $2.84 \times 10^6$ cells/mi and 4% paraformaldehyde dissolved in PBS to achieve a final concentration of 1% was added. After incubating for 30 min at room temperature (RT) on a rocker platform, equal volumes of PBS and 100 mM glycine were added and the mixture rocked for 5 min. The cells were spun down (1000 rpm, 5 min) and then resuspended in PBS+25 mM glycine and rocked for 15 min at RT. After spinning down (1000 rpm, 5 min) and resuspending in PBS and spinning down again (1000 rpm, 5 min), the cells were resuspended in 25 mM HEPES (pH 7.5) and stored at 2–8° C.

Figure 1:
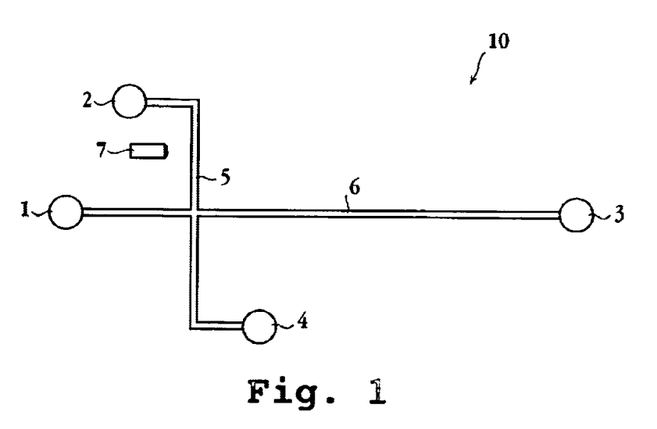
FIG. 1 is a diagrammatic view of a microfluidic device pattern.

A device is depicted diagrammatically in FIG. 1. The device 10 has wells 1, 2 3 and 4, and channels 5 and 6. A detector 7 observes the cells in channel 5. Each of the wells has an electrode, not shown. Reservoir 2 is the reservoir for the cells, while reservoirs 3 and 4 are waste reservoirs.

Figure 6:
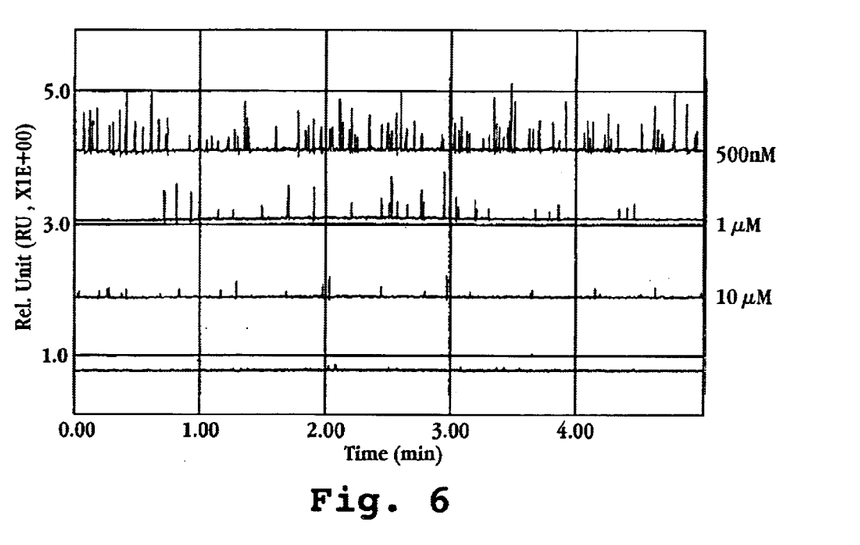
FIG. 6 is a graph of peaks resulting from the inhibition of fluorescent antagonist binding to NK-1 cells.
Figure 7:
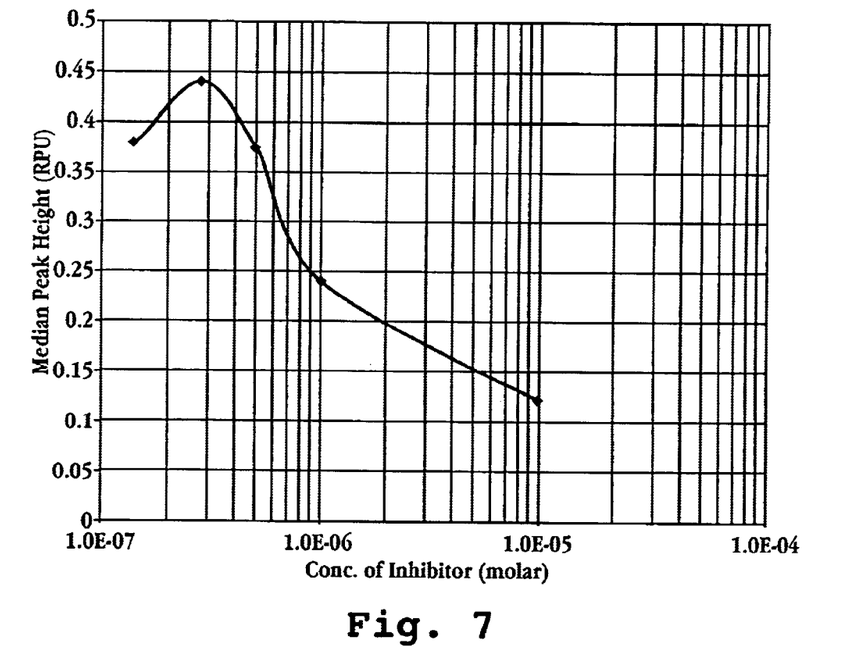
FIG. 7 is a line graph of the dose response of inhibition with fixed NK-1 cells.

The cells were introduced into reservoir 2 of a microfluidic device as depicted in FIG. 1. 3 μl of $1.5 \times 10^6$ cells were introduced into the well with Substance P labeled with Cy5 (140 nM) and varying concentrations of SAR-SP, an antagonist for the neurokinin receptor. The channel dimensions were 25×75 μm and the medium was 150 mM NaCl containing 0.5% PEO. The voltages were as follows, the initial number indicating the reservoir and the second number the voltage: 1, 338; 2, 70: 3, 0; and 4, 793. This voltage pattern provided a cell velocity of 44 cells/min past the detector. The detector was placed at a distance of 1.1 mm from well 2. The cells were found to move in an orderly fashion down the channel and a responsecurve obtained by measuring the mean peak height over a 5 min interval. The concentrations employed were 0, 10 μM, 1 μM and 500 nM. The observed mean peak heights (RFU) for the total number of cells observed over the 5 min interval were 0.13, 0.24, 0.37 and 0.45 and respectively. The results are as shown in FIG. 6 with a dose response curve shown in FIG. 7, where the dose response curve has two additional points. The data demonstrate that one can readily detect concentrations of ligand at or below 500 nM, with a fluorescent binding assay and obtain individual peaks, which may then be integrated to give an overall result.

The observation was that when no cell was present in the illuminated volume, a level of fluorescence corresponding to the unbound fluorescent-ligand was observed. As cells passed through he illuminated volume, a significant fluctuation in the fluorescent signal was observed. The fluctuations appear as sharp peaks and a quantity corresponding to the average extent of fluorescent ligand binding can be measured by averaging the integrated peak areas. The mean value varied inversely with the amount of antagonist present in the cell medium.

Figure 4:
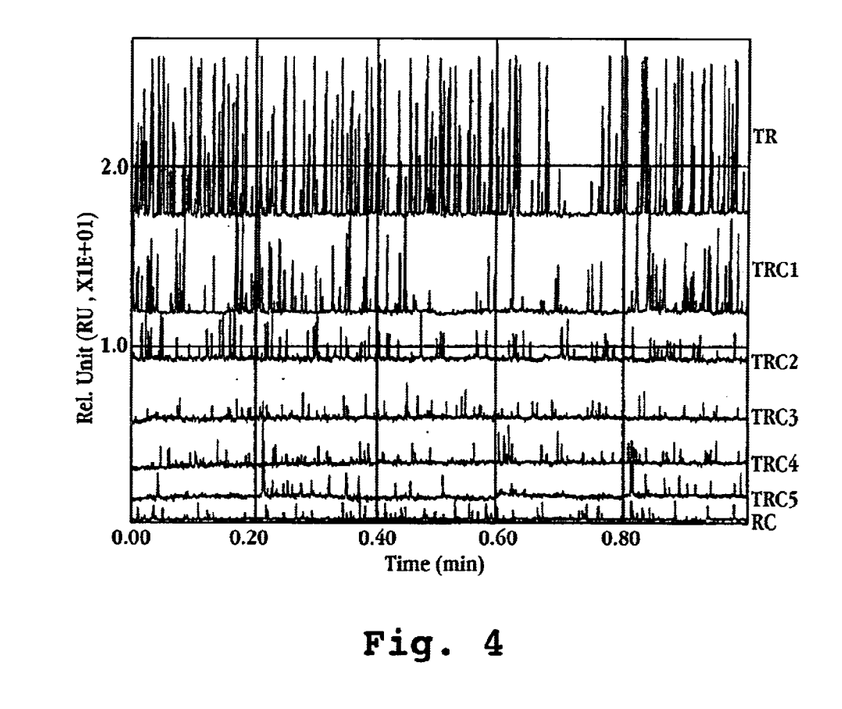
FIG. 4 is a graph of peaks resulting from the cytometric analysis of fluorescent
Figure 5:
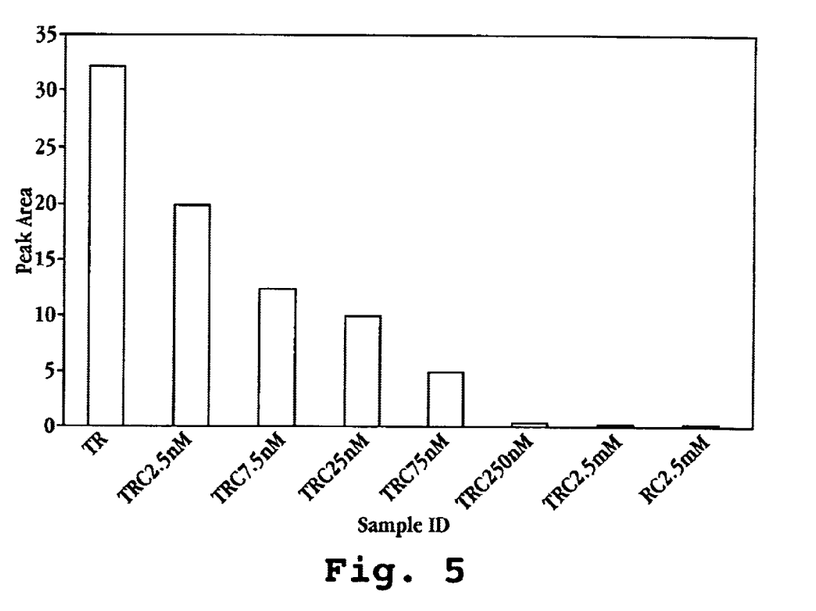
FIG. 5 is a bar graph of the inhibition of binding of fluorescent ligand by competing ligand.

In the next study, pumping means was employed to move cells through a capillary. The cells were cultured cells having a high level of the fMLP receptor on the surface. The buffer solution was 140 mM NaCl, 1 mM $KH_2PO_4$, 5 mM $Na_2HPO_4$, 1.5 mM $CaCl_2$, 0.3 mM $MgSO_4$, 1 mM $MgCl_2$, 0.2% BSA. The cell concentration in the reservoir was $10^6$/ml and the receptor concentration was 413 pM. The labeled ligand was fluorescein or Cy-5 labeled fMLPK (N-formyl-Met-Leu-Phe-Lys) which competed with fMLP for receptor. The labeled ligand was 4 nM, while the ligand concentration was varied from 2.5 nM to 250 nM. The device was comprised of a reservoir having a volume of 500 $\mu$l into which was introduced a capillary having an I.D. of 100 $\mu$m. In place of an electroosmotic pump, a syringe pump operating at 500 $\mu$l/min applied to the other end of the capillary was employed. The reading was taken at about 100 mm from the capillary inlet. The results are shown in FIGS. 4 and 5, where TR stands for tracer, RC refers to receptor and TRC refers to both Tracer and Receptor. The cytometric analysis and the bar graph of FIGS. 4 and 5 show the height and frequency of peaks with only tracer and only receptor and at various concentrations of ligand, where the bar graph shows the result for 2.5 mM in the presence and absence of tracer. At 2.5 mM of the ligand, there is substantially no signal. The results demonstrate that one can sensitively distinguish low concentrations of a ligand in the presence of a fluorescent tracer, obtaining signals as to individual cells and combining the results as a total peak area, with a clear differentiation between concentrations as low as 2.5 nM and differing by only 5 nM.

In and initial study for calibration, four solutions were prepared: (1) 25 $\mu$l buffer and 25 $\mu$l Cy5-fMLPK; (2) 25 $\mu$l cells and 25 $\mu$l 12 nM Cy5-fMLPK; (3) 25 $\mu$l cells and 25 $\mu$l 12 nM Cy5-fMLPK and 0.25 $\mu$l 1 mM fMLPK; and (4) 25 $\mu$l cells and 25 $\mu$l buffer. The flurescence was read with the aid of a P/ACE, which covers a volume of 50 $\mu$l. The as follows:

|   | A | B | C | D |
|---|---|---|---|---|
| 1 | 1.91, 1.93 | 1.88, 1.89 | 1.98, 1.99 | 1.95, 1.97 |
| 2 | 0.099, 0.097 | 0.088, 0.090 | 0.110, 0.103 | 0.117, 0.118 |
| 3 | 1,97, 1.99 | 1.98, 1.97 | 2.06, 2.06 | 1.95, 1.99 |
| 4 | 0.036, 0.039 | 0.033, 0.032 | 0.037, 0.037 | 0.037, 0.038 |

In the next study four solutions were prepared using the Cy-5 conjugate of fMLPK. The compositions are as follows: (1) 125 $\mu$l buffer and 125 $\mu$l Cy-5-fMLPK; (2) 125 $\mu$l Cy5-fMLPK and 125 $\mu$l cells; (3) 125 $\mu$l Cy-5-fMLPK, 125 $\mu$l cells and 1 $\mu$l 1 mM fMLPK; and 125 $\mu$l buffer and 125 $\mu$l cells. An Hitachi fluorimeter was used to read scence which covers 220 $\mu$l. For buffer, the readings were 34,33. The results are as follows:

|   | A | B | C | D |
|---|---|---|---|---|
| 1 | 859 | 836 | 800 | 768 |
| 2 | 69 |  | 67 |  |
| 3 | 844 |  | 826 | 812 |
| 4 | 29 | 24 | 29 | 27 |

In the following study using concentrations of the fMLPK of 0, 2.5 nM, 250 nM and 2.5 $\mu$M, following results were observed, respectively, reported as total peak height: 33, 19, <1, 0.

Figure 2:
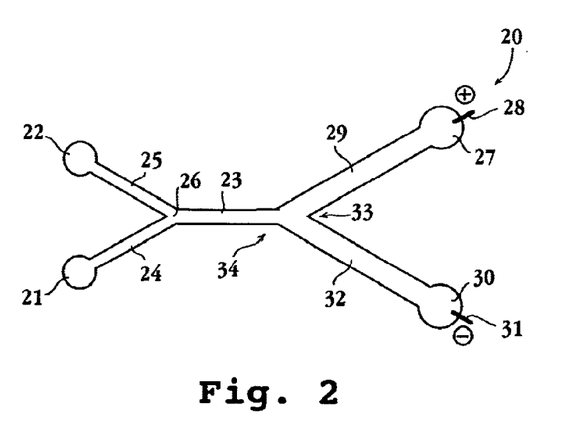
FIG. 2 is an alternative diagrammatic view of a microfluidic device pattern.

In FIG. 2 is depicted a diagrammatic view of a device using two legs for an electroosmotic pump. Device 20 has a cellular reservoir 21 and a reagent reservoir 22. Cellular reservoir 21 is connected to main channel 23 by channel 24, while reagent reservoir 22 is connected to main channel 23 by channel 25. Channels 23, 24 and 25 meet in a Y to create mixing region. The EOP is formed by reservoir 27 having positive electrode 28, which reservoir is connected to positively charged channel 29 and reservoir 30 with negatively charged electrode 31, which reservoir 30 is connected to negatively charged channel 32. Channels 29 and 32 are connected to main channel 23 at Y 33. As depicted, channels 29 and 32 have a greater cross-section than main channel 23, but all that is required is that the channels of the EOP be large enough to accommodate the flow of liquid from the main channel to provide the desired rate of flow of the cells in the main channel and the desired rate of mixing of the reagents and cells. By controlling the cross-sectional ratio of channels 24 and 25, the ratio of the volume of the cellular medium which is mixed with the reagent medium may be controlled. Alternatively, one may provide valves or other control means to control the ratio of the two media. In operation, the cellular media in reservoir 21 and the reagent media in reservoir 22 are buffered at an appropriate salt concentration for maintaining the viability of the cells. The medium in the main channel 23 and EOP channels 29 and 32 will be of much lower salt concentration for the electroosmotic pumping. By activating electrodes 28 and 31, flow will occur toward reservoirs 27 and 30, so that the cells in reservoir 21 and the reagents in reservoir 22 will move toward the main channel and mix at region 26. The cells will then move down channel 23 at a rate controlled by the voltage differential between electrodes 28 and 31 and move past detector 34, which will evaluate the effect of the reagents on the cells. By appropriate choice of cross-section of channel 24 and media for the cells, clumping and aggregation may be minimized and individual cells moved past the detector 34 to provide independent cytometric analysis.

Figure 3:
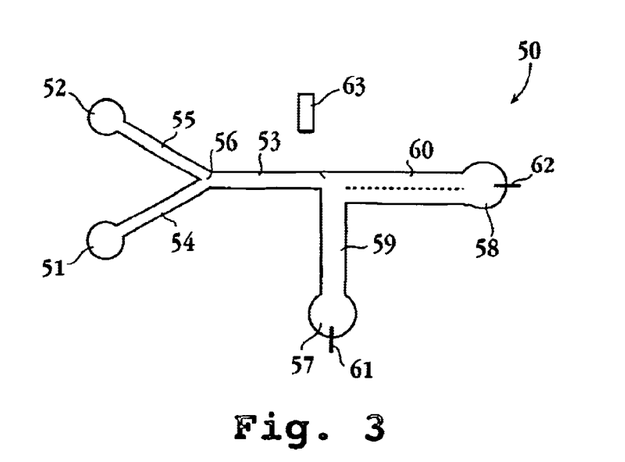
FIG. 3 is an alternative diagrammatic view of a microfluidic device pattern.

In FIG. 3, dynamic coating is employed for the EOP. The device 50 has a cell reservoir 51 and a reagent reservoir 52, with the former connected to main channel 53 through channel 54 and the latter connected to main channel 53 through channel 55, joining together at Y-junction 56 to form a mixing region. As discussed above, by controlling the cross-sectional ratio of channels 54 and 55, the ratio of mixing of the cellular media and reagent media will be defined. The EOP is formed by reservoirs 57 and 58 which are connected to main channel 53 by channels 59 and 60 respectively. Channel 60 will have a cross-section large enough to accommodate the flow of liquid from channels 53 and 59, where channel 53 has a cross-section large enough to accommodate the flow of liquid from channels 54 and 55. Thus, the flow from channel 60 into reservoir 58 controls the flow of fluid in the system. By varying the voltage between electrodes 61 and 62 and/or the concentration of the hydrophilic charged polymer in reservoir 57, one can vary the rate at which the cells and the reagents enter the mixing region 56. In the case of a positively charged polymer, the polarity of the device would be set up as follows. The electrode 61 would be negatively charged and reservoir 57 would have the polymer, which would also be included in channels 59 and 60. Electrode 62 would be negatively charged. The media in channels 59 and 60 and reservoirs 57 and 58 would have a salt concentration in the range of about 10 to 50 mM. Upon activating the electrodes 61 and 62, liquid would flow from reservoirs 51, 52 and 57 through channels 53 and 59 into channel 60. The cells after reaction with the reagents would move through channel 53 past detector 63. The operation could then be stopped, once the cells have been detected. Where there is a stream of individual cells, the detector could be placed at a site remote from the EOP, so that the cells need never enter the EOP region, although once the cells are past the detector, they will generally be discarded.

It is evident from the observed results that the use of microfluidic devices for performing operations on cells offers many advantages. Individual cells can be observed, so that one can average the results over a cell population, as well as observe the effect of an agent with cells having different states, such as different mitotic states. The device permits doing both equilibrium and kinetic studies, allows for the use of viable and fixed cells, and permits the use of very small amounts of reagents and small numbers of cells for the determinations.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for performing cell-based operations capable of identifying single cell status, employing a microfluidic device having (i) a reservoir containing cells for said cell-based operations, said reservoir containing an appropriate viable cell supporting medium, (ii) a first capillary channel in fluid transfer relationship with said reservoir, (iii) an electroosmotic pump comprising a second capillary channel in fluid receiving relationship with said first channel, (iv) an electrokinetic medium in said second capillary channel and (v) a pair of electrodes for creating an electrical field in said electrokinetic medium for moving electrokinetic medium in said second channel, and (vi) a detector, said method comprising:

at least prior to adding said cells to said reservoir, contacting said cells with a compound of interest that affects the status of said cells;

contacting said cells with a labeled ligand which competes with the compound of interest for binding to a cell receptor;

applying an electrical field to said electrokinetic medium in said second capillary channel in a direction to remove liquid from said first channel, whereby cells move from said reservoir into said first channel;

continuing removal of liquid from said first channel while moving said cells to the site of said detector, and determining the effect of said compound of interest on the status of said cells by measuring the amount of labeled ligand bound to said cells.

2. A method according to claim 1, wherein said cells are fixed cells.

3. A method according to claim 1, wherein said cells are viable cells.

4. A method according to claim 1, wherein said viable cell supporting medium is isotonic for said cells by the addition of a neutral osmolality enhancing agent to provide an osmolality in the range of about 250 to 350 mOsm.

5. A method for performing cell-based operations identifying single cell status, employing a microfluidic device having a reservoir containing cells for said cell-based operations, said reservoir containing an appropriate viable cell supporting medium, a first capillary channel in fluid transfer relationship with said reservoir, an electroosmotic pump comprising a second capillary channel in fluid receiving relationship with said first channel, an electrokinetic medium in said second capillary channel and a pair of electrodes for creating an electrical field in said electrokinetic medium for moving electrokinetic medium in said second channel, and a detector, said method comprising:

adding a labeled ligand by electrokinetic means into said first capillary channel to contact said cells, wherein said labeled ligand binds to a cell surface receptor of said cells;

applying an electrical field to said electrokinetic medium in said second capillary channel in a direction to remove liquid from said first channel, whereby cells move individually from said reservoir into said first channel;

adding by electrokinetic means into said first channel a compound of interest for contact in said first channel with said cells;

moving said cells to the site of said detector; and determining the effect of said compound on the status of said cells by detecting the presence of said labeled ligand.

6. A method according to claim 5, wherein said labeled ligand is a fluorescently labeled ligand and said detector is a fluorimeter.

7. A method according to claim 5, wherein said cells are genetically modified to produce a detectable product upon binding of a ligand to a cell surface receptor, and said determining comprises detecting the production of said detectable product.

8. A method according to claim 5, wherein said applying moves said cells by electroosmotic pumping, said pumping employing two legs of a channel, with each leg pumping liquid in an opposite direction, and an electric field is absent in the portion of the channel in which said cells are moved.

9. A method according to claim 8, wherein said cells are in a physiological medium.

10. A method according to claim 5, wherein said compound of interest is an antagonistand said determining is a result of variation in signal by cells displacing in said conductive medium a fluorescent agent binding to said cells.

11. A method for performing cell based operations identifying single cell status, employing a microfluidic device having a reservoir containing fixed cells for said cell based operations, a capillary channel in fluid transfer relationship with said reservoir, a pair of electrodes for creating an electrical field in a conductive medium for moving cells in said channel and a detector, said method comprising:

- at least prior to adding said cells to said reservoir, contacting said cells with an agent that affects the status of said cells;
- applying an electrical field to said conductive medium in said capillary channel, whereby cells individually move from said reservoir into said channel;
- moving said cells to the site of said detector; and
- determining the effect of said agent on the status of said cells.

12. A method according to claim 11, wherein said applying moves said cells electrophoretically and said channel comprises an electrophoretic medium containing less than 1% of a polymer matrix.

13. A method according to claim 11, wherein said agent is contacted with said cells in said channel.

14. A method according to claim 11, wherein said agent is labeled with a detectable label.

15. A method according to claim 11, wherein said agent is an antagonist and said determining is as a result of variation in signal by cells displacing in said conductive medium a fluorescent agent binding to said cells.

* * * * *